United States Patent
Buss et al.

(10) Patent No.: US 10,922,932 B2
(45) Date of Patent: Feb. 16, 2021

(54) ACOUSTIC USER INTERFACE

(71) Applicant: Roche Diabetes Care, Inc., Indianapolis, IN (US)

(72) Inventors: Beate Buss, Mannheim (DE); Sascha Kahl, Dortmund (DE); Sebastian Triesch, Dortmund (DE)

(73) Assignee: ROCHE DIABETES CARE, INC., Indianapolis, IN (US)

(*) Notice: Subject to any disclaimer, the term of this patent is extended or adjusted under 35 U.S.C. 154(b) by 0 days.

(21) Appl. No.: 16/347,883

(22) PCT Filed: Dec. 7, 2017

(86) PCT No.: PCT/EP2017/081897
§ 371 (c)(1),
(2) Date: May 7, 2019

(87) PCT Pub. No.: WO2018/104480
PCT Pub. Date: Jun. 14, 2018

(65) Prior Publication Data
US 2019/0287355 A1    Sep. 19, 2019

(30) Foreign Application Priority Data

Dec. 7, 2016   (EP) .................................... 16202763

(51) Int. Cl.
*C08K 3/00*     (2018.01)
*G08B 3/10*     (2006.01)
(Continued)

(52) U.S. Cl.
CPC ............... *G08B 3/10* (2013.01); *A61M 5/142* (2013.01); *G06F 3/167* (2013.01); *A61M 2205/581* (2013.01); *H04R 1/028* (2013.01)

(58) Field of Classification Search
CPC .......... G08B 25/016; G08B 5/36; G08B 7/06; G08B 15/004; G08B 21/02; G08B 21/18;
(Continued)

(56) References Cited

U.S. PATENT DOCUMENTS 8,585,638 B2    11/2013 Blomquist
8,773,257 B2 *  7/2014  Yodfat ............... A61M 5/14248
                                                  340/384.6
(Continued)

FOREIGN PATENT DOCUMENTS

EP       2 460 546 A1     6/2012
EP       2460546 A1 *     6/2012  ............ A61M 5/142

*Primary Examiner* — Munear T Akki
(74) *Attorney, Agent, or Firm* — Woodard, Emhardt, Henry, Reeves & Wagner, LLP

(57) ABSTRACT

The present invention relates to a method for guiding a user in interaction with an insulin pump comprising providing in response to a user interaction at least one of (i) a first acoustic signal comprising at least five descending halftones, wherein the duration of each tone is independently selected from a range of from 0.025 s to 5 s; (ii) a second acoustic signal comprising at least five ascending halftones, wherein the duration of each tone is independently selected from a range of from 0.025 s to 5 s; (iii) a third acoustic signal comprising at least seven ascending halftones, wherein the duration of each tone is independently selected from a range of from 0.025 s to 5 s; (iv) a fourth acoustic signal comprising at least two alternating tritones, wherein the duration of each tone is independently selected from a range of from 0.025 s to 5 s; (v) a fifth acoustic signal of four tones with a duration of from 0.025 s to 0.5 s, followed by a single tone with a duration of at least twofold of any one of the preceding four tones, wherein at least one tone of the acoustic signals of (i) to (v) has a frequency in the range of from 1500 Hz to 4000 Hz, in an embodiment of from 1700 Hz to 3800 Hz. Further, the present invention relates to (Continued)

Figure 1:
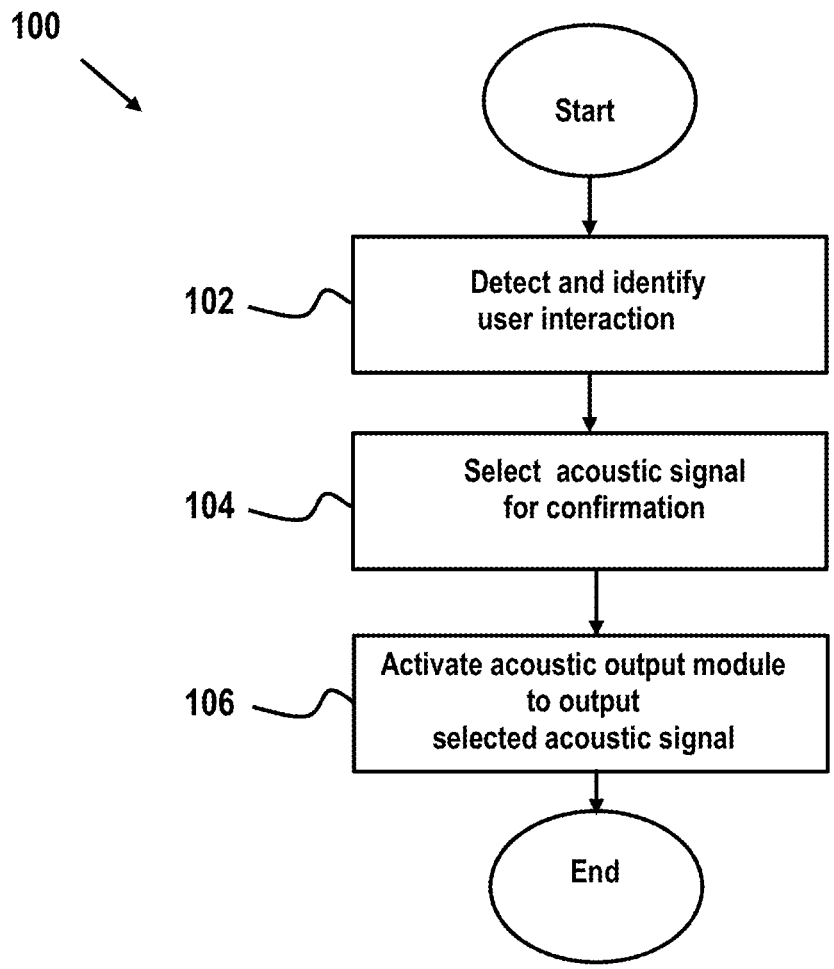

devices, computer program products, and uses related thereto.

14 Claims, 4 Drawing Sheets

(51) Int. Cl.
*A61M 5/142* (2006.01)
*G06F 3/16* (2006.01)
*H04R 1/02* (2006.01)

(58) Field of Classification Search
CPC .......... G08B 25/08; G08B 25/10; G08B 5/22; G08B 7/066; G08B 13/22; G08B 21/0446; G08B 21/24; G08B 3/10; A61M 5/142; A61M 2205/581; G06F 3/167; H04R 1/028
USPC .......................................................... 340/6.1
See application file for complete search history.

(56) References Cited

U.S. PATENT DOCUMENTS

| | | | |
|---|---|---|---|
| 9,907,943 B2 * | 3/2018 | Grant | A61M 5/14586 |
| 2009/0005726 A1 * | 1/2009 | Jones | A61M 5/142 |
| | | | 604/65 |
| 2009/0275886 A1 * | 11/2009 | Blomquist | G09G 3/3466 |
| | | | 604/66 |
| 2011/0201911 A1 * | 8/2011 | Johnson | G01N 33/66 |
| | | | 600/365 |
| 2014/0221966 A1 * | 8/2014 | Buckingham | A61M 5/14244 |
| | | | 604/504 |
| 2014/0276420 A1 * | 9/2014 | Rosinko | A61M 5/172 |
| | | | 604/151 |
| 2016/0254952 A1 * | 9/2016 | Harvey | H04L 41/0813 |
| | | | 715/735 |
| 2019/0287355 A1 * | 9/2019 | Buss | G08B 3/10 |
| 2019/0290173 A1 * | 9/2019 | Newberry | G16H 40/67 |

* cited by examiner

US 10,922,932 B2

ACOUSTIC USER INTERFACE

FIELD OF THE INVENTION

The present invention relates to a method for guiding a user in interaction with an insulin pump comprising providing in response to a user interaction at least one of (i) a first acoustic signal comprising at least five descending halftones, wherein the duration of each tone is independently selected from a range of from 0.025 s to 5 s; (ii) a second acoustic signal comprising at least five ascending halftones, wherein the duration of each tone is independently selected from a range of from 0.025 s to 5 s; (iii) a third acoustic signal comprising at least seven ascending halftones, wherein the duration of each tone is independently selected from a range of from 0.025 s to 5 s; (iv) a fourth acoustic signal comprising at least two alternating tritones, wherein the duration of each tone is independently selected from a range of from 0.025 s to 5 s; (v) a fifth acoustic signal of four tones with a duration of from 0.025 s to 0.5 s, followed by a single tone with a duration of at least twofold of any one of the preceding four tones, wherein at least one tone of the acoustic signals of (i) to (v) has a frequency in the range of from 1500 Hz to 4000 Hz, in an embodiment of from 1700 Hz to 3800 Hz. Further, the present invention relates to devices, computer program products, and uses related thereto.

RELATED ART

Medical devices for fluid delivery, e.g. insulin pumps, frequently include a notification component for notification purposes, e.g., to notify the user that fluid delivery has started and/or for alerting purposes (cf. e.g. US 2011/0221583 A1). Such notification components have been included the delivery device itself and/or in a remote control. The notification component can provide auditory signals (e.g., from a buzzer), visual signals (e.g., a display, flashing lights, etc.) or can provide tactile signals (e.g., from a vibrator). An auditory notification component ("buzzer") can employ, for example, a piezoelectric element or a magnetic element, which is typically disposed within a resonance chamber (i.e., a cavity defined by interior surfaces that reflect acoustic/sound waves) in order to amplify the sound generated by the element. For generating auditory signals, in particular piezoelectric elements or transducers have been used, since they require relatively little power.

U.S. Pat. No. 7,515,060 teaches the use of audible sounds provided by an insulin pump for assisting the user in navigating through the pump's menus. Similarly, US 2011/0221583 A1 teaches use of audible signal sequences representative of operating conditions of a therapeutic fluid dispensing device. U.S. Pat. Nos. 8,585,638 and 8,469,920 disclose insulin pumps with a bolus button and providing different audible signals assigned to different bolus amounts.

In a device for delivering a therapeutic fluid (e.g., insulin) to the body of a patient, it is generally important to provide unambiguous feedback, since the consequence of not interpreting the feedback correctly by the user can be hazardous. This problem becomes particularly pronounced in cases where the device is body-mounted and may not be easily accessible, and in particular where the device is additionally covered by e.g. clothing.

Problem to be Solved

There is, thus, a need in the art for improved methods for providing feedback to a user in user-device interactions, and for guiding a user in interaction with a medical device, in particular a body-mounted medical device.

This problem is solved by the means and methods of the present invention, with the features of the independent claims. Preferred embodiments, which might be realized in an isolated fashion or in any arbitrary combination are listed in the dependent claims.

Accordingly, the present invention relates to a method for guiding a user in interaction with an insulin pump comprising providing in response to a user interaction at least one of (i) a first acoustic signal comprising at least five, in an embodiment of at least seven, descending halftones, wherein the duration of each tone is independently selected from a range of from 0.025 s to 5 s, in an embodiment from a range of from 0.05 s to 0.5 s;
(ii) a second acoustic signal comprising at least five ascending halftones, wherein the duration of each tone is independently selected from a range of from 0.025 s to 5 s, in an embodiment from a range of from 0.05 s to 0.5 s;
(iii) a third acoustic signal comprising at least seven ascending halftones, wherein the duration of each tone is independently selected from a range of from 0.025 s to 5 s, in an embodiment from a range of from 0.05 s to 0.5 s;
(iv) a fourth acoustic signal comprising at least two, in an embodiment at least three, in a further embodiment at least four, alternating tritones, wherein the duration of each tone is independently selected from a range of from 0.025 s to 5 s, in an embodiment from a range of from 0.05 s to 0.5 s;
(v) a fifth acoustic signal of four tones with a duration of from 0.025 s to 0.5 s, followed by a single tone with a duration of at least twofold of any one of the preceding four tones, wherein at least one tone of the acoustic signals of (i) to (v) has a frequency in the range of from 1500 Hz to 4000 Hz, in an embodiment of from 1700 Hz to 3800 Hz.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, as used in the following, the terms "preferably", "more preferably", "most preferably", "particularly", "more particularly", "specifically", "more specifically" or similar terms are used in conjunction with optional features, without restricting further possibilities. Thus, features introduced by these terms are optional features and are not intended to restrict the scope of the claims in any way. The invention may, as the skilled person will recognize, be performed by using alternative features. Similarly, features introduced by "in an embodiment of the invention" or similar expressions are intended to be optional features, without any restriction regarding further embodiments of the invention, without any restrictions regarding the scope of the invention and without any restriction regarding the possibility of combining the features introduced in such way with other optional or non-optional features of the invention. Moreover, if not otherwise indicated, the term "about" relates to the indicated value with the commonly accepted technical precision in the relevant field, preferably relates to the indicated value±20%, more preferably ±10%, most preferably ±5%.

The method of the present invention is a non-diagnostic and a nontherapeutic method. Moreover, it may comprise steps in addition to those explicitly mentioned above. For example, further steps may relate, e.g., to providing further user guidance by one or more further acoustic, optical, or haptic signal. In an embodiment, the method is a method for avoiding erroneous interaction of the user with an insulin pump, in a further embodiment provides a fail-safe function. Thus, in an embodiment, upon providing at least one of the acoustic signals of the present invention, the insulin pump enters a state in which a correcting input by the user is accepted. In an embodiment, the method comprises providing in response to a user interaction at least two, in an embodiment at least three, in a further embodiment at least four, in a further embodiment at least the five acoustic signal as specified herein above. As will be understood by the skilled person, different acoustic signals are provided in response to different user interaction; thus, in an embodiment, a specific acoustic signal is assigned to a specific type of user interaction, such as initiating a task or a mode, or stopping a task or mode. In a further embodiment, a specific acoustic signal as specified herein is assigned to a specific user interaction, such as end of flight mode, incrementing bolus, and the like. Particular embodiments of acoustic signal/task or mode combinations are specified herein below.

If not otherwise noted, notation of individual tones is provided herein by scientific pitch notation (SPN), which is in principle known to the skilled person and which combines a musical note name with a number identifying the pitch's octave. Thus, e.g. a note C7 relates to the note C in the 7th octave of SPN. In an embodiment, the pitch referred to herein refers to a system based on an A4 having a frequency of from 438 Hz to 448 Hz, and further notes being assigned according to conventional interval rules. In an embodiment, the pitch referred to herein refers to a system based on an A4 having a frequency of 446 Hz. In a further embodiment, the pitch referred to herein refers to a system based on an A4 having a frequency of 440 Hz, as is the case in an equal tempered scale. In an embodiment, acoustic signals comprising at least one of A6 to DIS7 are based on an equally tempered scale, i.e. based on an A4 with a frequency of 440 Hz; in a further embodiment, acoustic signal comprising at least one of E7 to AIS7 are based on an A4 with a frequency of 446 Hz. As will be understood by the skilled person, the term "frequency" relates to the number of oscillations per time unit and is a measure for the pitch of a tone. As will be further understood by the skilled person, the term "tone", as used herein, refers to any type of audible signal of the indicated frequency range or frequency, including tones having sinus, rectangle, sawtooth, and triangle waves; in a further embodiment, the term includes complex tones, in particular sounds, having the indicated pitch. In an embodiment, the term tone relates to sounds in which the major amplitude is of the indicated frequency range or frequency. In an embodiment, the term refers to tones essentially having sinus waves, in a further embodiment, the term refers to tones having sinus waves.

The term "guiding a user", as used herein, relates to providing to a user information relevant for interaction with an insulin pump. In an embodiment, the term guiding a user relates to providing feedback on which state an insulin pump is in or is in the process of assuming, in particular in response to a user interaction, e.g. depression of a button. In a further embodiment, guiding a user is confirming to a user that a button or a combination of buttons eliciting a specific action by an insulin pump was pressed and/or confirming to the user that a specific action was initiated by an insulin pump.

The term "insulin pump" is known to the skilled person and relates to a device transferring insulin into the body of the subject. In an embodiment, the insulin pump is a programmable insulin pump, i.e. an insulin pump providing amounts of insulin to the subject predetermined by user and/or by a glucose management unit, such as a glucose meter, in particular a glucose meter connected to a unit calculating recommended insulin bolus. In an embodiment, the insulin pump is a body-mounted insulin pump, i.e. an insulin pump fixed to the surface of the body of the subject. In an embodiment, the insulin pump is an insulin pump fixed to a surface of the body difficult to reach by the subject, in particular the back or lower back of the subject. In an embodiment, the insulin pump is an insulin pump as described in US patent application 2011/022583 A1.

The term "user interaction", as used herein, relates to an action performed by a subject in order to achieve a change of state of an insulin pump and/or induction of a specific action by said insulin pump. In an embodiment, user interaction comprises providing at least one detectable signal to the insulin pump, such as a voice command, providing a signal via a remote control, or depressing at least one button. In an embodiment, user interaction is depressing at least one button; in a further embodiment, user interaction is depressing one button or is depressing two buttons simultaneously or successively.

As used herein, the term "response to a user interaction" relates to providing a signal detectable by a user by an insulin pump as a sign that the user interaction was registered by the insulin pump. Accordingly, a response to a user interaction, in an embodiment, is a confirmation of the user interaction.

The term acoustic signal, as used herein, relates to an audible signal generated by an insulin pump. As is understood by the skilled person, an acoustic signal may simply consist of a short tone of a single frequency. In an embodiment, an acoustic signal comprises at least two different tones played in succession. In a further embodiment, the acoustic signal is played by the insulin pump at a sound pressure level of at least 40 dB, in an embodiment at least 40 dB(A), in an embodiment at least 45 dB, in an embodiment at least 45 dB(A). In a further embodiment, the acoustic signal is played by the insulin pump at a sound pressure level of at most 70 dB, in an embodiment 70 dB(A), in a further embodiment at most 60 dB, in an embodiment at most 60 dB(A). In a further embodiment, the acoustic signal is played by the insulin pump at a sound pressure level of from 40 dB to 70 dB, in an embodiment of from 40 dB(A) to 70 dB(A), in a further embodiment of from 45 dB to 60 dB, in an embodiment of from 45 dB(A) to 60 dB(A). In a further embodiment, the acoustic signal is played by the insulin pump at a sound pressure level of about 45 dB, in an embodiment about 45 dB(A). As is further understood by the skilled person, the acoustic signal, in an embodiment, has a frequency in the range which can be perceived by a subject; thus, in case the subject is a human, the acoustic signal comprises at least one tone of a frequency in the range of from 500 Hz to 10,000 Hz, in an embodiment of from 1500 Hz to 4000 Hz, in a further embodiment of from 1700 Hz to 3800 Hz. In a further embodiment, all tones comprised in the acoustic signal have a frequency in the range of from 500 Hz to 10,000 Hz, in an embodiment of from 1500 Hz to 4000 Hz, in a further embodiment of from 1700 Hz to 3800 Hz.

In an embodiment, the duration of at least one tone of an acoustic signal according to the present invention is at least 50 ms, in an embodiment at least 100 ms; thus, in an embodiment, the duration of at least one tone of an acoustic signal is in the range of from 0.025 s to 5 s, in an embodiment of from 0.05 s to 0.5 s. In a further embodiment, the duration of all tones of an acoustic signal is selected from a range of from 0.025 s to 5 s, in an embodiment of from 0.05 s to 0.5 s.

In an embodiment, a first acoustic signal provided by an insulin pump comprises at least five, an embodiment at least seven, descending half tones, wherein the duration of each tone is independently selected from a range of from 0.025 s to 5 s, in an embodiment from a range of from 0.05 s to 0.5 s. In an embodiment, the duration of all tones of the first acoustic signal is selected from the range of from 0.05 s to 0.25 s, in an embodiment of from 0.075 s to 0.15 s, in a further embodiment is about 0.1 s, in a further embodiment is 100 ms. In a further embodiment, all tones of the first acoustic signal have the same duration, in particular a duration as specified herein above. In an embodiment, the first of the descending halftones of the first acoustic signal has a frequency in the range of from 2200 Hz to 4000 Hz, in an embodiment is a GIS7, an A7, or an AIS7, in a further embodiment has a frequency of about 3780 Hz, in a further embodiment is an AIS7. Thus, in an embodiment, the first acoustic signal comprises, in an embodiment consists of, the acoustic signal AIS7, A7, GIS7, G7, FIS7, F7, E7. In a further embodiment, the first acoustic signal comprises, in an embodiment is AIS7, A7, GIS7, G7, FIS7, F7, E7, each with a duration of 100 ms. In a further embodiment, the first of the descending halftones of the first acoustic signal is a CIS7, a D7, or a DIS7, in a further embodiment has a frequency of about 2489 Hz, in a further embodiment is a DIS7. Thus, in an embodiment, the first acoustic signal comprises, in an embodiment consists of, the acoustic signal DIS7, D7, CIS7, C7, B6, AIS6, A6. In a further embodiment, the first acoustic signal comprises, in an embodiment consists of, the acoustic signal DIS7, D7, CIS7, C7, B6, AIS6, A6 and each tone of said acoustic signal has a duration of 100 ms. In an embodiment, a first acoustic signal as specified above is provided to confirm stopping of a mode or of a task, in an embodiment is provided to confirm ending of a flight mode. Thus, in an embodiment, upon providing the first acoustic signal, the insulin pump proceeds to stopping a mode or a task, in an embodiment stops a flight mode.

In an embodiment, a second acoustic signal provided by an insulin pump comprises at least five ascending halftones, wherein the duration of each tone is independently selected from a range of from 0.025 s to 5 s, in an embodiment from a range of from 0.05 s to 0.5 s. In an embodiment, the duration of the first four of the ascending halftones of the second acoustic signal is selected from the range of from 0.1 s to 0.5 s, in an embodiment of from 0.15 s to 0.25 s, in a further embodiment is about 0.2 s, in a further embodiment is 200 ms; in an embodiment, the duration of the fifth tone of the ascending halftones is selected from the range of from 0.2 s to 0.8 s, in an embodiment of from 0.3 s to 0.5 s, in a further embodiment is about 0.4 s, in a further embodiment is 400 ms. In a further embodiment, the first four of the ascending halftones of the second acoustic signal have the same duration, in particular a duration as specified herein above. In an embodiment, the first tone of the second acoustic signal has a frequency in the range of from 1700 Hz to 3000 Hz, in an embodiment is an E7, an F7, or a FIS7, in a further embodiment has a frequency of about 2673 Hz, in a further embodiment is an E7. In a further embodiment, the second acoustic signal comprises, in an embodiment consists of, the acoustic signal E7, F7, FIS7, G7, GIS7. In a further embodiment, the second acoustic signal comprises, in an embodiment consists of, the acoustic signal E7, F7, FIS7, G7, GIS7, wherein the tones E7, F7, FIS7, G7 have a duration of 200 ms and wherein the tone GIS7 has a duration of 400 ms. In an embodiment, the first of the ascending halftones of the second acoustic signal is an A6, AIS6, or a B6, in an embodiment has a frequency of about 1760 Hz, in a further embodiment is an A6. In a further embodiment, the second acoustic signal comprises, in an embodiment consists of, the acoustic signal A6, AIS6, B6, C7, CIS7. In a further embodiment, the second acoustic signal comprises, in an embodiment consists of, the acoustic signal A6, AIS6, B6, C7, and CIS7, wherein the tones A6, AIS6, B6, C7 have a duration of 200 ms and the tone CIS7 has a duration of 400 ms. In an embodiment, the second acoustic signal is provided to confirm start of a mode or of execution of a task. In a further embodiment, upon providing said second acoustic signal, the insulin pump proceeds to entering a predefined mode or to executing a predefined task. Thus, in an embodiment, the second acoustic signal is provided to confirm start of execution of a task, in an embodiment a predefined task.

In an embodiment, a third acoustic signal provided by an insulin pump comprises at least seven ascending halftones, wherein the duration of each tone is independently selected from a range of from 0.025 s to 5 s, in an embodiment from a range of from 0.05 s to 0.5 s. In an embodiment, the duration of the ascending halftones of the third acoustic signal is independently selected from the range of from 0.05 s to 0.5 s, in an embodiment of from 0.05 s to 0.15 s, in a further embodiment is about 0.1 s, in a further embodiment is 100 ms. In a further embodiment, the ascending halftones of the third acoustic signal have the same duration, in particular a duration as specified herein above. In an embodiment, the first of the ascending halftones of the third acoustic signal has a frequency in the range of from 1700 Hz to 3000 Hz, in an embodiment is an E7, an F7, or a FIS7, in a further embodiment has a frequency of about 2673 Hz, in a further embodiment is an E7. In an embodiment, the third acoustic signal comprises, in an embodiment consists of, the acoustic signal E7, F7, FIS7, G7, GIS7, A7, AIS7. In a further embodiment, the second acoustic signal comprises, in an embodiment consists of, the acoustic signal E7, F7, FIS7, G7, GIS7, A7, AIS7 and each tone of said acoustic signal has a duration of 100 ms. In an embodiment, the first of the ascending halftones of the third acoustic signal is an A6, an AIS6, or a B6, in an embodiment has a frequency of about 1760 Hz, in a further embodiment is an A6. In a further embodiment, the third acoustic signal comprises, in an embodiment consists of, the acoustic signal A6, AIS6, B6, C7, CIS7, D7, DIS7. In a further embodiment, the third acoustic signal comprises, in an embodiment consists of, the acoustic signal A6, AIS6, B6, C7, CIS7, D7, DIS7 and each tone of said acoustic signal has a duration of 100 ms. In an embodiment, the third acoustic signal is provided to confirm start of a mode or of execution of a task. In a further embodiment, upon providing said third acoustic signal, the insulin pump proceeds to entering a predefined mode or to executing a predefined task. In an embodiment, the third acoustic signal is provided to confirm start of a mode, in an embodiment of a quick bolus mode. Thus, in an embodiment, upon providing the third acoustic signal, the insulin pump proceeds to entering a quick bolus mode.

In an embodiment, a fourth acoustic signal provided by an insulin pump comprises at least two, in an embodiment at least three, in a further embodiment at least four, alternating tritones, wherein the duration of each tone is independently selected from a range of from 0.025 s to 5 s, in an embodiment from a range of from 0.05 s to 0.5 s. In an embodiment, the duration of the tones of the fourth acoustic signal is selected from the range of from 0.05 s to 0.5 s, in an embodiment of from 0.05 s to 0.15 s, in a further embodiment is about 0.1 s, in a further embodiment is 100 ms. In a further embodiment, the tones of the fourth acoustic signal have the same duration, in particular a duration as specified herein above. In an embodiment, the first of the alternating tritones is an ascending tritone. In an embodiment, the first tone of the alternating tritones of the fourth acoustic signal has a frequency of in the range of from 3250 Hz to 4000 Hz, in an embodiment is a GIS7, an A7, or an AIS7, in a further embodiment has a frequency of about 3780 Hz, in a further embodiment is an AIS7. In an embodiment, the fourth acoustic signal comprises, in an embodiment consists of the acoustic signal AIS7, E7, AIS7, in an embodiment AIS7, E7, AIS7, E7, AIS7. In a further embodiment, the first acoustic signal comprises, in an embodiment consists of the acoustic signal AIS7, E7, AIS7, in an embodiment AIS7, E7, AIS7, E7, AIS7 and each tone of said acoustic signal has a duration of 100 ms. In an embodiment, the first tone of the fourth acoustic signal is a DIS7, a D7, or a CIS7, in a further embodiment has a frequency of about 2489 Hz, in a further embodiment is a DIS7. In a further embodiment, the fourth acoustic signal comprises, in an embodiment consists of the acoustic signal DIS7, A6, DIS7, in an embodiment DIS7, A6, DIS7, A6, DIS7. In a further embodiment, the fourth acoustic signal comprises, in an embodiment consists of, the acoustic signal DIS7, A6, DIS7, in an embodiment DIS7, A6, DIS7, A6, DIS7 and each tone of said acoustic signal has a duration of 100 ms. In an embodiment, the fourth acoustic signal is provided to confirm cancellation of a user interaction or of a task. In a further embodiment, upon providing said fourth acoustic signal, the insulin pump proceeds to cancelling execution of the task instantly executed. In a further embodiment, upon providing said fourth acoustic signal, the insulin pump proceeds to cancelling the most recent user interaction.

In an embodiment, a fifth acoustic signal is provided by an insulin pump of four tones with a duration of from 0.025 s to 0.5 s, followed by a single tone with a duration of at least twofold of any one of the preceding four tones. In an embodiment, the first four tones of the fifth acoustic signal have the same duration. In an embodiment, the first tone of the fifth acoustic signal has a frequency in the range of from 3000 Hz to 4000 Hz, in an embodiment is a FIST, a G7, a GIS7, an A7, or an AIS7, in a further embodiment has a frequency of about 3368 Hz, in a further embodiment is a GIS7. In a further embodiment, all tones of the fifth acoustic signal have the same frequency, in an embodiment are GIS7. In an embodiment, the fifth acoustic signal comprises, in an embodiment consists of tones of the same frequency, in an embodiment of GIS7s and the first four tones of the fifth acoustic signal have a duration of 200 ms and the fifth tone of said fifth acoustic signal has a duration of 400 ms. In an embodiment, the first tone of the fifth acoustic signal is a B6, a C7, a CIS7, an D7, or a DIS7, in a further embodiment has a frequency of about 2217 Hz, in a further embodiment is a CIS7. In a further embodiment, the fifth acoustic signal comprises, in an embodiment consists of tones of the same frequency, in an embodiment of CIS7s and the first four tones of the fifth acoustic signal have a duration of 200 ms and the fifth tone of said fifth acoustic signal has a duration of 400 ms. In an embodiment, the fifth acoustic signal is provided to confirm five depression events of a user operable button, in an embodiment of an insulin bolus increment button. In a further embodiment, upon providing said fifth acoustic signal, said insulin pump proceeds to providing an insulin bolus to the user.

The term "flight mode" is understood by the skilled person and relates to a mode of an insulin pump in which wireless communication of the pump with external devices is reduced or switched off completely. Accordingly, in flight mode, an insulin pump typically can only be managed by direct interaction with user operable buttons comprised by the pump itself. As a consequence, also signaling to the pump that flight mode shall be ended ("end of flight mode") can only be signaled to the pump by depressing one or more user operable buttons on the insulin pump.

The terms "mode" and "task" are also understood by the skilled person. A mode, as used herein, is a state of a device characterized by specific settings; e.g. flight mode, as specified herein above, is a mode in which communication with external devices is reduced or switched off. A task, as used herein, relates to an action an insulin pump is programmed to perform.

The term "insulin bolus" is known to the skilled person to relate to a batch amount of insulin which is administered to a subject in case a hyperglycemic event is registered or if such an event is anticipated. E.g. a calculated insulin bolus is typically administered to a subject before a meal to compensate for carbohydrate uptake during said meal. The term "insulin bolus increment button", correspondingly, relates to a user operable button which allows the user to increase, in an embodiment in discrete steps, the amount of insulin administered; thus, each depression event of the insulin bolus increment button increases the amount of insulin administered by an arbitrary or pre-defined unit.

In an embodiment, the method for guiding a user in interaction with an insulin pump comprises providing a first acoustic signal as specified herein above to confirm stopping of a mode or of a task and providing a second and/or third acoustic signal as specified herein above to confirm start of a mode or of execution of a task. In a further embodiment, the method for guiding a user in interaction with an insulin pump comprises providing a first acoustic signal as specified herein above to confirm stopping of a mode or of a task and providing a fourth acoustic signal as specified herein above to confirm cancellation of a user interaction or of a task. In a further embodiment, the method for guiding a user in interaction with an insulin pump comprises providing a first acoustic signal as specified herein above to confirm stopping of mode or of a task and providing a fifth acoustic signal as specified herein above to confirm five depression events of a user operable button. In a further embodiment, the method for guiding a user in interaction with an insulin pump comprises providing a second and/or third acoustic signal as specified herein above to confirm start of a mode or of execution of a task and providing a fourth acoustic signal as specified herein above to confirm cancellation of a user interaction or of a task. In a further embodiment, the method for guiding a user in interaction with an insulin pump comprises providing a second and/or third acoustic signal as specified herein above to confirm start of a mode or of execution of a task and providing a fifth acoustic signal as specified herein above to confirm five depression events of a user operable button. In a further embodiment, the method for guiding a user in interaction with an insulin pump comprises providing a fourth acoustic signal as specified herein above to confirm cancellation of a user interaction or of a task and providing a fifth acoustic signal as specified herein above to confirm five depression events of a user operable button. In a further embodiment, the method for guiding the user in interaction with an insulin pump comprises providing a first acoustic signal as specified herein above to confirm stopping of a mode or of a task, providing a second and/or third acoustic signal as specified herein above confirm start of a mode or of execution of a task, and providing a fourth acoustic signal as specified herein above to confirm cancellation of a user interaction or of a task. In a further embodiment, the method for guiding a user in interaction with an insulin pump comprises providing a first acoustic signal as specified herein above to confirm stopping of a mode or of a task, providing a second and/or third acoustic signal as specified herein above to confirm start of a mode or of execution of a task, and providing a fifth acoustic signal specified herein above to confirm five depression events of the user operable button. In a further embodiment, the method for guiding the user in interaction with an insulin pump comprises providing a first acoustic signal as specified herein above to confirm stopping of a mode or of a task, providing a second and/or third acoustic signal as specified herein above to confirm start of a mode or of execution of a task, providing a fourth acoustic signal as specified herein above to confirm cancellation of a user interaction or of a task, and providing a fifth acoustic signal specified herein above to confirm five depression events of a user operable button.

It is, however, also envisaged that the method for guiding a user in interaction with an insulin pump comprises providing additional acoustic signals, in particular providing a single tone (beep) to indicate legal, i.e. permitted, depression of a button. In an embodiment, the duration of said tone is in range of from 0.1 s to 0.5 s, in an embodiment of from 0.15 s to 0.25 s, in a further embodiment is about 0.2 s, in a further embodiment is 200 ms. In an embodiment, the frequency of the tone provided by the insulin pump to confirm a legal depression event is in the range of from 1700 Hz to 3000 Hz, in an embodiment is an E7, an F7 or FIST, in a further embodiment is an E7, in further embodiment is an A6, an AIS6, or a B6, in a further embodiment is an A6.

Advantageously, it was found in the work underlying the present invention that insulin pumps, which may be mounted on body regions not easily accessible by a user, and which may additionally be covered by several layers of clothing, require particularly well audible user interaction signals. Besides sound volume, pitch and melody of signals were found to be important factors for providing unambiguous user interaction signals. Moreover, it was found in the work underlying the present invention that some combinations of intervals (melodies) are easier to remember than others. Since user interaction signals of insulin pumps are required by the user only very infrequently, using user interaction signals which can be easily remembered even over long time intervals increases safety of user/pump interaction. Moreover, at a sound pressure level of approximately 45 dB, it was found that the signals are loud enough to be perceived, but not too loud to disturb the surrounding.

The definitions made above apply mutatis mutandis to the following. Additional definitions and explanations made further below also apply for all embodiments described in this specification mutatis mutandis.

The present invention further relates to an insulin pump comprising a controller module, a user input module, and an acoustic output module, wherein said controller module, user input module, and acoustic output module are functionally linked, and wherein said control unit is adapted to cause the acoustic output module to output at least one of the acoustic signals according to the present invention in response to a user input.

The term "controller module" relates to any module comprised in an insulin pump adapted to receive information that user input, in particular depression of a user-operable button, was detected, optionally verifying that such user input is legal, i.e. permissible, at the current state of the insulin pump, and causing the acoustic output unit to output at least one of the acoustic signals according to the present invention. In an embodiment, the controller module comprises or is a microprocessor. In an embodiment, the controller module is adapted to control the pumping function of the insulin pump.

As used herein, the term "user input module" includes any module suitable of receiving an input from a user, including in particular wireless receivers receiving user input from an external device, e.g. a remote control or a smartphone, and user-operable buttons. User-operable buttons are known to the skilled person. In an embodiment, the user-operable button is a mechanical button, in an embodiment providing haptic feedback, e.g. by providing a perceivable pressure point. In an embodiment, the insulin pump comprises at least two user-operable buttons.

The term "acoustic output module", as used herein, includes all modules suitable to generate tones as specified herein. In an embodiment, the acoustic output module comprises a vibratory membrane coupled to an oscillation inducer. In an embodiment, the acoustic output module is an electrodynamic acoustic output module, an electrostatic acoustic output module, or a piezoelectric acoustic output module (piezo element). In an embodiment, the acoustic output module is a piezoelectric acoustic output module. Suitable piezoelectric acoustic output modules are known to the skilled person. In an embodiment, the acoustic output module is adapted to provide at least two different tones with a frequency in the range of from 1500 Hz to 4000 Hz, in an embodiment of from 1700 Hz to 3800 Hz. In a further embodiment, the acoustic output module is adapted to provide at least five, in an embodiment at least seven, different tones with a frequency in the range of from 1500 Hz to 4000 Hz, in an embodiment of from 1700 Hz to 3800 Hz.

As will be understood, the insulin pump comprises a pump module mediating delivery of insulin to the subject.

Moreover, the present invention relates to the use of at least one acoustic signal of the acoustic signals of the present invention for guiding a user in the use of an insulin pump.

The invention further discloses and proposes a computer program including computer-executable instructions for performing the method according to the present invention in one or more of the embodiments enclosed herein when the program is executed on a controller module of an insulin pump. Specifically, the computer program may be stored on a computer-readable data carrier, e.g. a memory module functionally linked with a controller module. Thus, specifically, one, more than one or even all of method steps and/or acoustic signals as indicated above may be performed by using a controller module of an insulin pump, preferably by using a computer program.

The invention further discloses and proposes a computer program product having program code means, in order to perform the method according to the present invention in one or more of the embodiments enclosed herein when the program is executed on a controller module of an insulin pump. Specifically, the program code means may be stored on a computer-readable data carrier.

Thus, the present invention also relates to a computer program product, a user input module, and an acoustic output module, said computer program product receiving user input from the user input module and assigning at least one specific user input to a predetermined acoustic signal of the acoustic signals of the present invention. In an embodiment, the computer program product further elicits output of the predetermined acoustic signal in response to the user input received. Thus, in an embodiment, the computer program product further causes the acoustic output module to provide said predetermined acoustic signal to the user. In an embodiment, the computer program product is tangibly embedded in a controller module of an insulin pump or in a memory module functionally linked to said controller module.

Further, the invention discloses and proposes a data carrier having a data structure stored thereon, which, after loading into a controller module of an insulin pump, such as into a working memory or main memory of a microprocessor comprised in said controller module, may execute the method according to one or more of the embodiments disclosed herein.

The invention further proposes and discloses a computer program product with program code means stored on a machine-readable carrier, in order to perform the method according to one or more of the embodiments disclosed herein, when the program is executed on a controller module of an insulin pump. As used herein, a computer program product refers to the program as a tradable product. The product may generally exist in an arbitrary format, such as in a paper format, or on a computer-readable data carrier. Specifically, the computer program product may be distributed over a data network.

Finally, the invention proposes and discloses a modulated data signal which contains instructions readable by a controller module of an insulin pump, for performing the method according to one or more of the embodiments disclosed herein.

Preferably, referring to the computer-implemented aspects of the invention, one or more of the method steps an/or acoustic signals or even all of the method steps and/or acoustic signals of the method according to one or more of the embodiments disclosed herein may be performed by using a controller module of an insulin pump.

Specifically, the present invention further discloses:

A controller module of an insulin pump comprising at least one processor, wherein the processor is adapted to perform the method according to one of the embodiments described in this description, a computer loadable data structure that is adapted to perform the method according to one of the embodiments described in this description while the data structure is being executed on an insulin pump, a computer program, wherein the computer program is adapted to perform the method according to one of the embodiments described in this description while the program is being executed on an insulin pump, a computer program comprising program means for performing the method according to one of the embodiments described in this description while the computer program is being executed on an insulin pump, a computer program comprising program means according to the preceding embodiment, wherein the program means are stored on a storage medium readable to a controller module of an insulin pump, a storage medium, wherein a data structure is stored on the storage medium and wherein the data structure is adapted to perform the method according to one of the embodiments described in this description after having been loaded into a main and/or working storage of a controller module of an insulin pump, and a computer program product having program code means, wherein the program code means can be stored or are stored on a storage medium, for performing the method according to one of the embodiments described in this description, if the program code means are executed on a controller module of an insulin pump.

Summarizing the findings of the present invention, the following embodiments are particularly envisaged:

1. A method for guiding a user in interaction with an insulin pump comprising providing in response to a user interaction at least one of (i) a first acoustic signal comprising at least five, in an embodiment of at least seven, descending halftones, wherein the duration of each tone is independently selected from a range of from 0.025 s to 5 s, in an embodiment from a range of from 0.05 s to 0.5 s;

(ii) a second acoustic signal comprising at least five ascending halftones, wherein the duration of each tone is independently selected from a range of from 0.025 s to 5 s, in an embodiment from a range of from 0.05 s to 0.5 s;

(iii) a third acoustic signal comprising at least seven ascending halftones, wherein the duration of each tone is independently selected from a range of from 0.025 s to 5 s, in an embodiment from a range of from 0.05 s to 0.5 s;

(iv) a fourth acoustic signal comprising at least two, in an embodiment at least three, in a further embodiment at least four, alternating tritones, wherein the duration of each tone is independently selected from a range of from 0.025 s to 5 s, in an embodiment from a range of from 0.05 s to 0.5 s; and (v) a fifth acoustic signal of four tones with a duration of from 0.025 s to 0.5 s, followed by a single tone with a duration of at least twofold of any one of the preceding four tones, wherein at least one tone of the acoustic signals of (i) to (v) has a frequency in the range of from 1500 Hz to 4000 Hz, in an embodiment of from 1700 Hz to 3800 Hz.

2. The method of embodiment 1, wherein all tones of acoustic signals (i) to (v) have a frequency in the range of from 1500 Hz to 4000 Hz, in an embodiment of from 1700 Hz to 3800 Hz.

3. The method of embodiment 1 or 2, wherein the duration of all tones of the first acoustic signal, of the third acoustic signal, of the fourth acoustic signal, and of the fifth acoustic signal is selected from the range of from 0.05 s to 0.25 s, in an embodiment of from 0.75 s to 0.15 s, in a further embodiment is about 0.1 s, in a further embodiment is 100 ms.

4. The method of any one of embodiments 1 to 3, wherein all tones of the first acoustic signal, of the third acoustic signal, of the fourth acoustic signal, and/or the first four tones of the fifth acoustic signal have the same duration.

5. The method of any one of embodiments 1 to 4, wherein the first of the descending halftones of the first acoustic signal has a frequency of in the range of from 2200 Hz to 4000 Hz.

6. The method of any one of embodiments 1 to 5, wherein the first of the descending halftones of the first acoustic signal is a GIS7, an A7, or an AIS7, in an embodiment has a frequency of about 3780 Hz, in a further embodiment is an AIS7.

7. The method of any one of embodiments 1 to 6, wherein the first acoustic signal comprises, in an embodiment consists of, the acoustic signal AIS7, A7, GIS7, G7, FIS7, F7, E7.

8. The method of any one of embodiments 1 to 7, wherein the first of the descending halftones of the first acoustic signal is a CIS7, an D7, or a DIS7, in a further embodiment has a frequency of about 2489 Hz, in a further embodiment is a DIS7.

9. The method of any one of embodiments 1 to 8, wherein the first acoustic signal comprises, in an embodiment consists of, the acoustic signal DIS7, D7, CIS7, C7, B6, AIS6, A6.

10. The method of any one of embodiments 1 to 9, wherein the first acoustic signal (i) comprises, in an embodiment consists of, the acoustic signal AIS7, A7, GIS7, G7, FIS7, F7, E7 or the acoustic signal DIS7, D7, CIS7, C7, B6, AIS6, A6; and (ii) wherein each tone of said acoustic signal has a duration of 100 ms.

11. The method of any one of embodiments 1 to 10, wherein said first acoustic signal is provided to confirm stopping of a mode or of a task, in an embodiment is provided to confirm ending of a flight mode.

12. The method of any one of embodiments 1 to 11, wherein, upon providing said first acoustic signal, said insulin pump proceeds to stopping a mode or a task, in an embodiment stops a flight mode.

13. The method of any one of embodiments 1 to 12, wherein said second and/or third acoustic signal is provided to confirm start of a mode or of execution of a task.

14. The method of any one of embodiments 1 to 13, wherein, upon providing said second and/or third acoustic signal, said insulin pump proceeds to entering a predefined mode or to executing a predefined task.

15. The method of any one of embodiments 1 to 14, wherein the first of the ascending halftones of the second acoustic signal has a frequency in the range of from 1700 Hz to 3000 Hz.

16. The method of any one of embodiments 1 to 15, wherein the first of the ascending halftones of the second acoustic signal is an E7, an F7, or a FIS7, in an embodiment has a frequency of about 2673 Hz, in a further embodiment is an E7.

17. The method of any one of embodiments 1 to 16, wherein said second acoustic signal comprises, in an embodiment consists of, the acoustic signal E7, F7, FIS7, G7, GIS7.

18. The method of any one of embodiments 1 to 15, wherein the first of the ascending halftones of the second acoustic signal is an A6, AIS6, or a B6, in an embodiment has a frequency of about 1760 Hz, in a further embodiment is an A6.

19. The method of any one of embodiments 1 to 15 or 18, wherein said second acoustic signal comprises, in an embodiment consists of, the acoustic signal A6, AIS6, B6, C7, CIS7.

20. The method of any one of embodiments 1 to 19, wherein said second acoustic signal comprises, in an embodiment consists of, (i) the acoustic signal E7, F7, FIS7, G7, GIS7, wherein the tones E7, F7, FIS7, and G7 have a duration of 200 ms and wherein the tone GIS7 has a duration of 400 ms; or (ii) the acoustic signal A6, AIS6, B6, C7, and CIS7, wherein the tones A6, AIS6, B6, C7 have a duration of 200 ms and wherein the tone CIS7 has a duration of 400 ms.

21. The method of any one of embodiments 1 to 20, wherein said second acoustic signal is provided to confirm start of execution of a task.

22. The method of any one of embodiments 1 to 21, wherein, upon providing said second acoustic signal, said insulin pump proceeds to executing a predefined task.

23. The method of any one of embodiments 1 to 22, wherein the first of the ascending halftones of the third acoustic signal has a frequency in the range of from 1700 Hz to 3000 Hz.

24. The method of any one of embodiments 1 to 23, wherein the first of the ascending halftones of the third acoustic signal is an E7, an F7, or a FIS7, in a further embodiment has a frequency of about 2673 Hz, in a further embodiment is an E7.

25. The method of any one of embodiments 1 to 24, wherein said third acoustic signal comprises, in an embodiment consists of, the acoustic signal E7, F7, FIS7, G7, GIS7, A7, AIS7.

26. The method of any one of embodiments 1 to 23, wherein the first of the ascending halftones of the third acoustic signal is an A6, an AIS6, or a B6, in an embodiment has a frequency of about 1760 Hz, in a further embodiment is an A6.

27. The method of any one of embodiments 1 to 23 or 26, wherein said third acoustic signal comprises, in an embodiment consists of, the acoustic signal A6, AIS6, B6, C7, CIS7, D7, DIS7.

28. The method of any one of embodiments 1 to 27, wherein said third acoustic signal (i) comprises, in an embodiment consists of, the acoustic signal E7, F7, FIS7, G7, GIS7, A7, AIS7 or the acoustic signal A6, AIS6, B6, C7, CIS7, D7, DIS7 and (ii) wherein each tone of said acoustic signal has a duration of 100 ms.

29. The method of any one of embodiments 1 to 28, wherein said third acoustic signal is provided to confirm start of a mode, in an embodiment of a quick bolus mode.

30. The method of any one of embodiments 1 to 29, wherein, upon providing said third acoustic signal, said insulin pump proceeds to entering a quick bolus mode.

31. The method of any one of embodiments 1 to 30, wherein the first tone of the fourth acoustic signal has a frequency of in the range of from 2400 Hz to 4000 Hz.

32. The method of any one of embodiments 1 to 31, wherein the first tone of the fourth acoustic signal is a GIST, an A7, or an AIS7, in a further embodiment has a frequency of about 3780 Hz, in a further embodiment is an AIS7.

33. The method of any one of embodiments 1 to 32, wherein the fourth acoustic signal comprises, in an embodiment consists of the acoustic signal AIS7, E7, AIS7, in an embodiment AIS7, E7, AIS7, E7, AIS7.

34. The method of any one of embodiments 1 to 31, wherein the first tone of the fourth acoustic signal is a DIS7, a D7, or a CIS7, in a further embodiment has a frequency of about 2489 Hz, in a further embodiment is a DIS7.

35. The method of any one of embodiments 1 to 31 or 34, wherein the fourth acoustic signal comprises, in an embodiment consists of the acoustic signal DIS7, A6, DIS7, in an embodiment DIS7, A6, DIS7, A6, DIS7.

36. The method of any one of embodiments 1 to 35, wherein the fourth acoustic signal (i) comprises, in an embodiment consists of, the acoustic signal AIS7, E7, AIS7, in an embodiment AIS7, E7, AIS7, E7, AIS7; or comprises, in an embodiment consists of, the acoustic signal DIS7, A6, DIS7, in an embodiment DIS7, A6, DIS7, A6, DIS7 and (ii) wherein each tone of said acoustic signal has a duration of 100 ms.

37. The method of any one of embodiments 1 to 36, wherein said fourth acoustic signal is provided to confirm cancellation of a user interaction or of a task.

38. The method of any one of embodiments 1 to 37, wherein, upon providing said fourth acoustic signal, said insulin pump proceeds to cancelling execution of the task instantly executed.

39. The method of any one of embodiments 1 to 38, wherein the first tone of the fifth acoustic signal has a frequency in the range of from 1900 Hz to 4000 Hz.

40. The method of any one of embodiments 1 to 39, wherein the first tone of the fifth acoustic signal is a FIST, a G7, a GIS7, an A7, or an AIS7, in a further embodiment has a frequency of about 3368 Hz, in a further embodiment is a GIS7.

41. The method of any one of embodiments 1 to 40, wherein all tones of the fifth acoustic signal have the same frequency, in an embodiment are GIS7.

42. The method of any one of embodiments 1 to 40, wherein the first tone of the fifth acoustic signal is a B6, a C7, a CIS7, an D7, or an DIS7, in a further embodiment has a frequency of about 2217 Hz, in a further embodiment is a CIS7.

43. The method of any one of embodiments 1 to 42, wherein the fifth acoustic signal comprises, in an embodiment consists of tones of the same frequency, in an embodiment of GIS7s or CIS7s and wherein the first four tones of the fifth acoustic signal have a duration of 200 ms and wherein the fifth tone of said fifth acoustic signal has a duration of 400 ms.

44. The method of any one of embodiments 1 to 43, wherein said fifth acoustic signal is provided to confirm five depression events of a user operable button, in an embodiment of an insulin bolus increment button.

45. The method of any one of embodiments 1 to 44, wherein, upon providing said fifth acoustic signal, said insulin pump proceeds to providing an insulin bolus to the user.

46. The method of any one of embodiments 1 to 45, wherein said method is a method for avoiding erroneous interaction of the user with the insulin pump, in an embodiment provides a fail-safe function.

47. The method of any one of embodiments 1 to 46, wherein, upon providing at least one of the acoustic signals of (i) to (v), the insulin pump enters a state in which a correcting input by the user is accepted.

48. The method of any one of embodiments 1 to 47, wherein said insulin pump is a body surface mounted insulin pump.

49. An insulin pump comprising a controller module, a user input module, and an acoustic output module, wherein said controller module, user input module, and acoustic output module are functionally linked, and wherein said control unit is adapted to cause the acoustic output module to output at least one of the acoustic signals according to embodiments 1 to 48 in response to a user input.

50. The insulin pump according to embodiment 49, wherein said acoustic output module is adapted to provide at least two different tones with a frequency in the range of from 1500 Hz to 4000 Hz, in an embodiment of from 1700 Hz to 3800 Hz.

51. The insulin pump according to embodiment 49 or 50, wherein said acoustic output module is adapted to provide at least five, in an embodiment at least seven, different tones with a frequency in the range of from 1500 Hz to 4000 Hz, in an embodiment of from 1700 Hz to 3800 Hz.

52. The insulin pump according to any one of embodiments 49 to 51, wherein said acoustic output module is a loudspeaker or a piezo element, in an embodiment is a piezo element.

53. The insulin pump according to any one of embodiments 49 to 52, wherein said user input module comprises at least one user-operable button.

54. The insulin pump according to any one of embodiments 49 to 53, wherein said user input module comprises at least two user-operable buttons.

55. The insulin pump according to any one of embodiments 49 to 54, wherein said controller module is further adapted to control the pumping function of the insulin pump.

56. The insulin pump according to any one of embodiments 49 to 55, wherein said insulin pump is a body surface mounted insulin pump.

57. A computer program product, in an embodiment tangibly embedded in a controller module of an insulin pump comprising a controller module, a user input module, and an acoustic output module, said computer program product receiving user input from the user input module and assigning at least one specific user input to a predetermined acoustic signal of the acoustic signals of any one of embodiments 1 to 48.

58. The computer program product of embodiment 57, wherein said computer program product further causes the acoustic output module to provide said predetermined acoustic signal to the user.

59. Use of at least one acoustic signal of the acoustic signals of embodiments 1 to 48 for guiding a user in the use of an insulin pump.

60. The method of any one of embodiments 1 to 48,
  wherein said first acoustic signal is provided to confirm stopping of a mode or of a task, in an embodiment is provided to confirm ending of a flight mode;
  wherein said second and/or third acoustic signal is provided to confirm start of a mode or of execution of a task;
  wherein said fourth acoustic signal is provided to confirm cancellation of a user interaction or of a task; and/or
  wherein said fifth acoustic signal is provided to confirm five depression events of a user operable button, in an embodiment of an insulin bolus increment button.

All references cited in this specification are herewith incorporated by reference with respect to their entire disclosure content and the disclosure content specifically mentioned in this specification.

FIGURE LEGENDS

FIG. 1: Exemplary signal election procedure.

Figure 2:
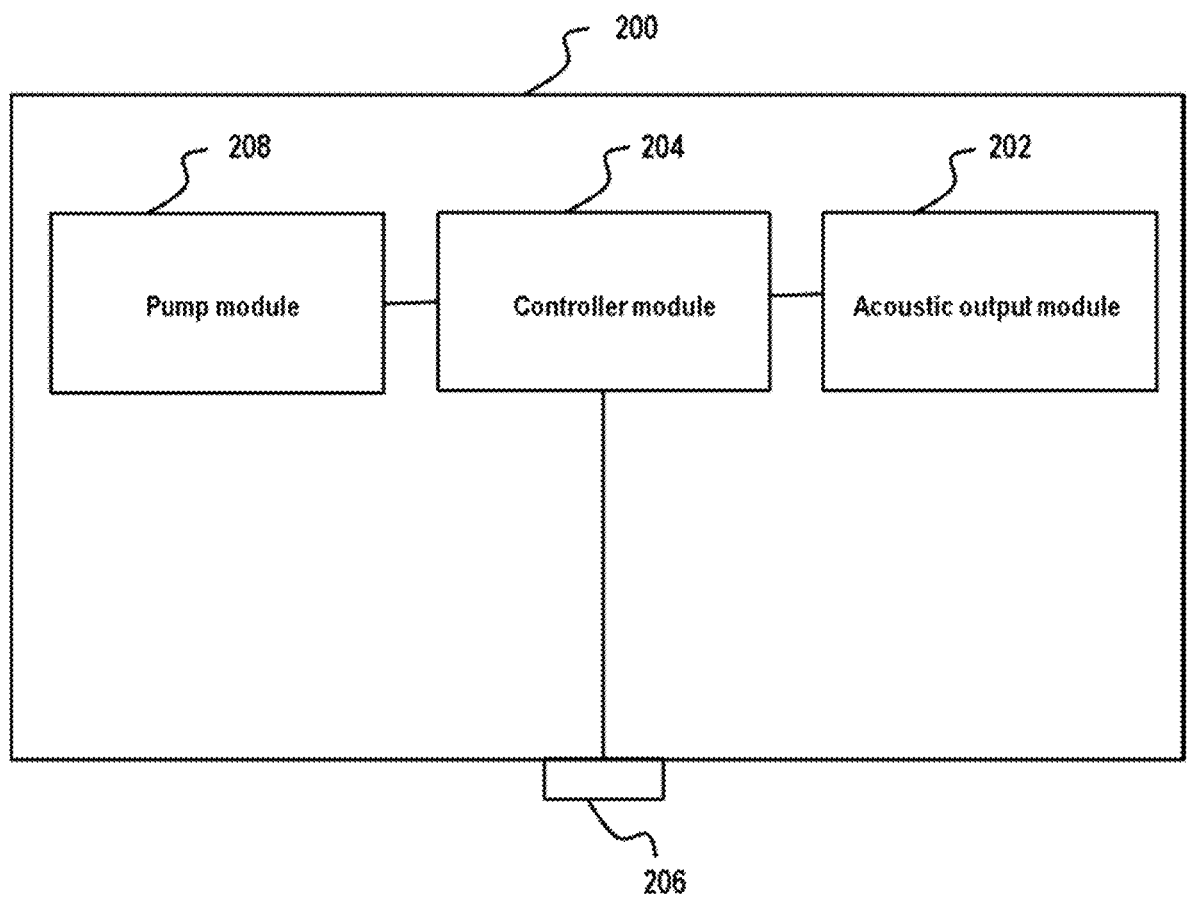

FIG. 2: Schematic insulin pump embodying features of the present invention

Figure 3:
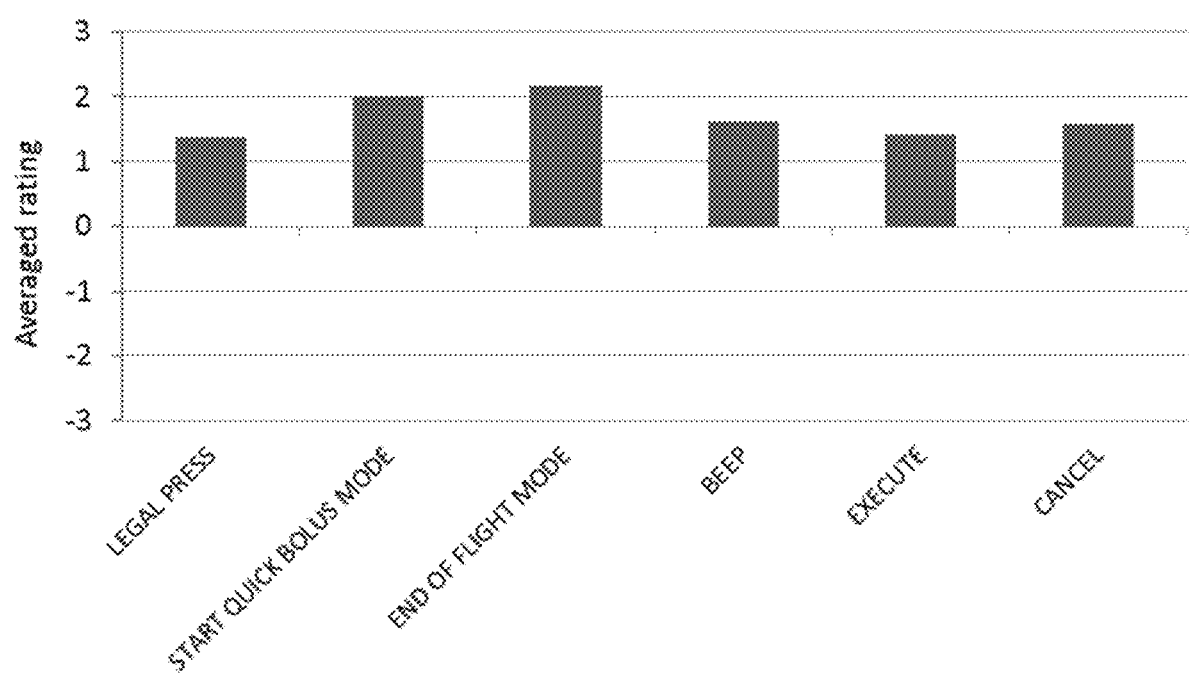

FIG. 3: Rating of signals regarding suitability (rating scale from −3 (not suitable) to +3 (fully suitable)).

Figure 4:
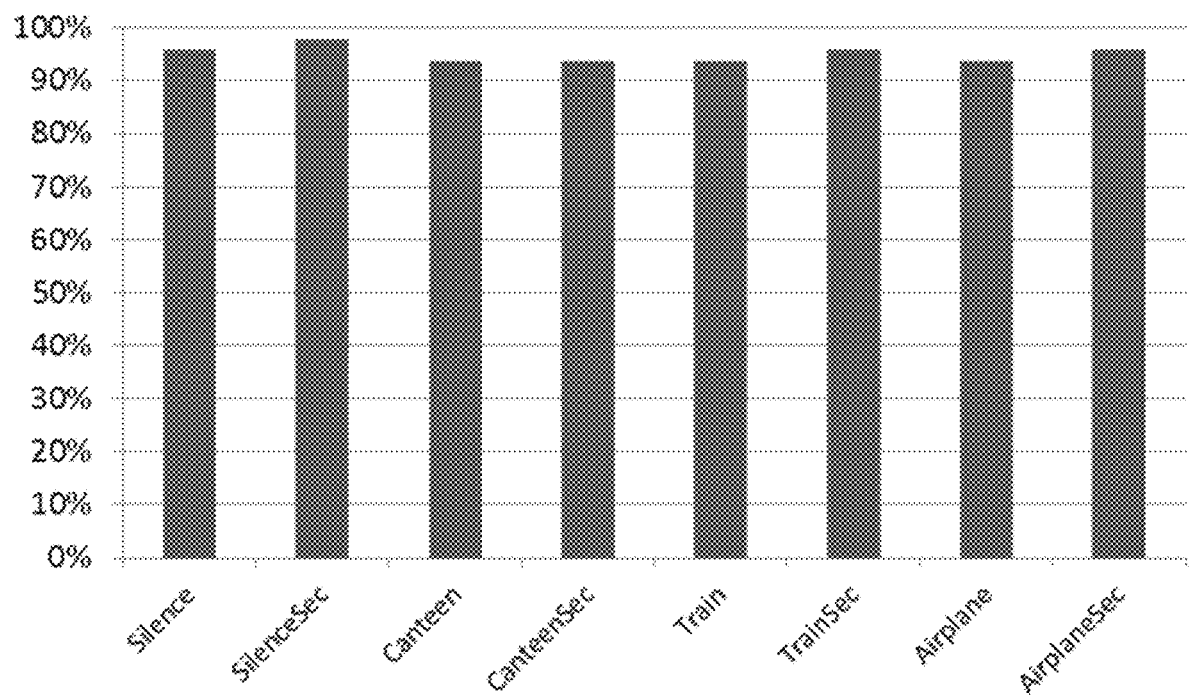

FIG. 4: Rates of correct interaction with a prototypical device in dependence on background noise as indicated; columns labelled " . . . Sec" relate to tests in which additionally a secondary task was to be fulfilled (solving a visual task, cf. Example 4); Y-axis: rate of correct user interaction.

The following Examples shall merely illustrate the invention. They shall not be construed, whatsoever, to limit the scope of the invention.

In an embodiment, the method of the present invention comprises a signal election procedure 100 as shown in FIG. 1. Therein, a user interaction is identified 102, e.g. by a controller module. Based on the user interaction and, optionally, the current state of the insulin pump, an appropriate signal is selected for outputting 104. Thereafter, the acoustic output module is activated to output the selected acoustic signal 106.

In an embodiment, the method of the present invention is implemented in an insulin pump having at least the features described in FIG. 2: The insulin pump comprises a housing 200, an acoustic output module 202, a controller module 204, at least one user-operable button 206, and a pump module 208.

EXAMPLE 1

The acoustic signals evaluated in the following experiments consisted of the following tones: E7 (2673 Hz), F7 (2832 Hz), FIS7 (3000 Hz), G7 (3178 Hz), GIS7 (3368 Hz), A7 (3568 Hz), and AIS7 (3780 Hz) as sinus tones.

The signals evaluated were (with D(X) indicating the duration of the tone in X ms):
EXECUTE (E7, D(200); F7, D(200); FIS7 D(200); G7 D(200); GIS7 D(400);
START QUICK BOLUS MODE (E7, D(100); F7, D(100); FIS7, D(100); G7, D(100); GIS7, D(100); A7, D(100); AIS7, D(100);
CANCEL (AIS7, D(100); E7, D(100); AIS7, D(100); E7, D(100)); AIS7, D(100);
END OF FLIGHT MODE (AIS7, D(100); A7, D(100); GIS7, D(100); G7, D(100); FIS7, D(100); F7, D(100); E7, D(100); and
BEEP (confirmation of pump increments in quick bolus mode): GIS(400) for each fifth, tenth, 15th, . . . increment, GIS7(200) for each intermediate increment.

22 Test subjects were elected, with a median age of 25 years (minimum age 18 years, maximal age 66 years); of the subjects, 6 were female and 16 were male.

EXAMPLE 2

In a first experiment, test subjects were asked to listen to the signals in arbitrary succession and to evaluate which function they would intuitively ascribe to the respective signal. After this, test subjects were made familiar with the actual assignment of the signals to the respective function and were asked to indicate on a scale of from −3 (unsuitable) to +3 (fully suitable), how suitable they evaluated the respective signal/function assignment. The results are shown in FIG. 3 and indicate that the selected signals were found to be very suitable by the test subjects.

EXAMPLE 3

In a second experiment, the test subjects of Example 2 were asked to listen to the various signals in arbitrary succession and in the context of various kinds of simulated ambient noise (airplane, canteen, or train). Test subjects were asked to provide an evaluation whether they were of the opinion that they perceived one of the signals and, in case yes, which of the signals they were of the opinion to have perceived. Success rate for all signals in tests for more quiet environments (silence and canteen) varied from 86%-97%.

For a specific task mode (programming of a quick bolus), an additional perception test was conducted. Test subjects (n=16) were asked to program a quick bolus and, in a second set of tests, additionally had to solve a visual task as distractor. As can be derived from FIG. 4, in interaction with a prototypical device the task was solved correctly in more than 90% of the tests, even in the presence of ambient noise and of a visual distraction. Thus, the signals tested are highly suitable to provide unambiguous user feedback, even on the background of ambient noise.

EXAMPLE 4

In a further test, signals comprising tones A6 (1760 Hz), AIS6 (1864 Hz), B6 (1975 Hz), C7 (2093 Hz), CIS7 (2217 Hz), D7 (2349 Hz), and DIS7 (2489 Hz) are evaluated, the acoustic signals being:
EXECUTE: A6, D(200); AIS6, D(200); B6 D(200); C7 D(200); CIS7 D(400);
START QUICK BOLUS MODE: (A6, D(100); AIS6, D(100); B6, D(100); C7, D(100); CIS7, D(100); D7, D(100); DIS7, D(100);
CANCEL: DIS7, D(100); A6, D(100); DIS7, D(100); A6, D(100)); DIS7, D(100);
END OF FLIGHT MODE: (DIS7, D(100); D7, D(100); CIS7, D(100); C7, D(100); B6, D(100); AIS6, D(100); A6, D(100); and
BEEP: CIS(400) for each fifth, tenth, 15th, . . . increment, CIS7(200) for each intermediate increment.

LIST OF REFERENCE SIGNS 100 signal election procedure
102 detection and identification of user interaction
104 selection of acoustic signal for confirmation
106 activation of acoustic output
200 insulin pump
202 acoustic output module
204 controller module
206 user input module, e.g. user-operable button
208 pump module

The invention claimed is:
1. A method for guiding a user in interaction with an insulin pump comprising:
guiding the user by providing to the user an acoustic signal in response to a first user interaction and an acoustic signal in response to a second user interaction, each acoustic signal representing either a state which the insulin pump is in or a state which the insulin pump is in a process of assuming, each acoustic signal comprising at least one of:
(i) a first acoustic signal comprising at least five descending halftones, wherein a duration of each halftone is independently selected from a range of from 0.025 s to 5 s;
(ii) a second acoustic signal comprising at least five ascending halftones, wherein the duration of each halftone is independently selected from a range of from 0.025 s to 5 s;
(iii) a third acoustic signal comprising at least seven ascending halftones, wherein the duration of each halftone is independently selected from a range of from 0.025 s to 5 s;
(iv) a fourth acoustic signal comprising at least two alternating tritones, wherein the duration of each tritone is independently selected from a range of from 0.025 s to 5 s; and
(v) a fifth acoustic signal of four tones, wherein the duration of each tone is independently selected from a range of from 0.025 s to 0.5 s, followed by a single tone with a duration of at least twofold of any one of the preceding four tones,
wherein at least one tone of the acoustic signals of (i) to (v) has a frequency in a range of from 1500 Hz to 4000 Hz.
2. The method of claim 1, wherein the duration of all tones of the first acoustic signal, of the third acoustic signal, of the fourth acoustic signal, and of the fifth acoustic signal is selected from the range of from 0.05 s to 0.25 s.

3. The method of claim 1, wherein the first of the descending halftones of the first acoustic signal has a frequency of in the range of from 2200 Hz to 4000 Hz.

4. The method of claim 1, wherein the first acoustic signal (i) comprises the acoustic signal AIS7, A7, GIS7, G7, FIS7, F7, E7 or the acoustic signal DIS7, D7, CIS7, C7, B6, AIS6, A6; and (ii) wherein each tone of said acoustic signal has a duration of 100 ms.

5. The method of claim 1, wherein the first of the ascending halftones of at least one of the second acoustic signal and the third acoustic signal has a frequency in the range of from 1700 Hz to 3000 Hz.

6. The method of claim 1, wherein said second acoustic signal comprises (i) the acoustic signal E7, F7, FIS7, G7, GIS7, wherein the tones E7, F7, FIS7, and G7 have a duration of 200 ms and wherein the tone GIS7 has a duration of 400 ms, or (ii) the acoustic signal A6, AIS6, B6, C7, and CIS7, wherein the tones A6, AIS6, B6, C7 have a duration of 200 ms and wherein the tone CIS7 has a duration of 400 ms.

7. The method of claim 1, wherein said third acoustic signal (i) comprises the acoustic signal E7, F7, FIS7, G7, GIS7, A7, AIS7 or the acoustic signal A6, AIS6, B6, C7, CIS7, D7, DIS7 and (ii) wherein each tone of said acoustic signal has a duration of 100 ms.

8. The method of claim 1, wherein the first tone of the fourth acoustic signal has a frequency of in the range of from 2400 Hz to 4000 Hz.

9. The method of claim 1, wherein the fourth acoustic signal (i) comprises the acoustic signal AIS7, E7, AIS7 or the acoustic signal DIS7, A6, DIS7, and (ii) wherein each tone of said acoustic signal has a duration of 100 ms.

10. The method of claim 1, wherein the first tone of the fifth acoustic signal has a frequency in the range of from 1900 Hz to 4000 Hz.

11. The method of claim 1, wherein the fifth acoustic signal comprises tones of the same frequency, and wherein the first four tones of the fifth acoustic signal have a duration of 200 ms and wherein the fifth tone of said fifth acoustic signal has a duration of 400 ms.

12. The method of claim 1, wherein said first acoustic signal is provided to confirm stopping of a mode or of a task;
wherein said second and/or third acoustic signal is provided to confirm start of a mode or of execution of a task;
wherein said fourth acoustic signal is provided to confirm cancellation of a user interaction or of a task; and/or
wherein said fifth acoustic signal is provided to confirm five depression events of a user operable button.

13. An insulin pump comprising:
a controller module;
a user interaction module; and
an acoustic output module, said controller module, user interaction module, and acoustic output module being functionally linked together,
said acoustic output module being configured to provide an acoustic signal representing either the state which the insulin pump is in or the state which the insulin pump is in the process of assuming, the acoustic signal comprising at least one of:
(i) a first acoustic signal comprising at least five descending halftones, wherein the duration of each halftone is independently selected from a range of from 0.025 s to 5 s;
(ii) a second acoustic signal comprising at least five ascending halftones, wherein the duration of each halftone is independently selected from a range of from 0.025 s to 5 s;
(iii) a third acoustic signal comprising at least seven ascending halftones, wherein the duration of each halftone is independently selected from a range of from 0.025 s to 5 s;
(iv) a fourth acoustic signal comprising at least two alternating tritones, wherein the duration of each tritone is independently selected from a range of from 0.025 s to 5 s; and
(v) a fifth acoustic signal of four tones, wherein the duration of each tone is independently selected from a range of from 0.025 s to 0.5 s, followed by a single tone with a duration of at least twofold of any one of the preceding four tones,
wherein at least one tone of the acoustic signals of (i) to (v) has a frequency in the range of from 1500 Hz to 4000 Hz;
said controller module being adapted to cause the acoustic output module to output at least one of the acoustic signals in response to a first user interaction, and to output at least one of the acoustic signals in response to a second user interaction.

14. The insulin pump of claim 13 wherein said acoustic output module is adapted to provide at least five different tones with a frequency in the range of from 1500 Hz to 4000 Hz.

* * * * *